United States Patent [19]

Cohn et al.

[11] Patent Number: 5,100,992
[45] Date of Patent: Mar. 31, 1992

[54] POLYURETHANE-BASED POLYMERIC MATERIALS AND BIOMEDICAL ARTICLES AND PHARMACEUTICAL COMPOSITIONS UTILIZING THE SAME

[75] Inventors: Daniel Cohn, Jerusalem; Shlomo Yitzchaiek, Ramat Gan; Sophie Bilenkis, Jerusalem, all of Israel

[73] Assignee: Biomedical Polymers International, Ltd., Guilderland, N.Y.

[21] Appl. No.: 520,059

[22] Filed: May 3, 1990

[30] Foreign Application Priority Data

May 4, 1989 [IL] Israel .......................... 90193

[51] Int. Cl.$^5$ .......................... C08G 18/10
[52] U.S. Cl. .......................... 528/26; 528/28; 528/59; 528/65; 424/501; 604/8; 604/19; 604/73; 604/93; 604/289; 604/290; 604/327; 604/403
[58] Field of Search .......... 528/26, 28, 59, 65; 424/501; 604/8, 19, 73, 93, 289, 290, 327, 403

[56] References Cited

U.S. PATENT DOCUMENTS 4,267,299  5/1981  Oechsle .......................... 528/59

*Primary Examiner*—Maurice J. Welsh
*Attorney, Agent, or Firm*—Fleit, Jacobson, Cohn, Price, Holman & Stern

[57] ABSTRACT

The invention provides a polyurethane amide segmented copolymer selected from:

a) a segmented block polyurethane amide (PEUAm) of the following repeating unit [I]

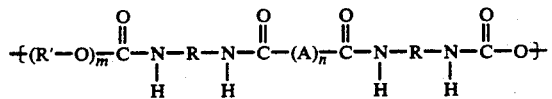

b) a segmented block polyurethane amide of the following repeating unit [II]

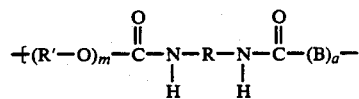

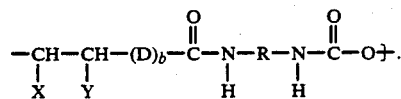

26 Claims, No Drawings

POLYURETHANE-BASED POLYMERIC MATERIALS AND BIOMEDICAL ARTICLES AND PHARMACEUTICAL COMPOSITIONS UTILIZING THE SAME

The present invention relates to new and useful polyurethane-based polymeric materials, derived from reacting flexible diol chains with diisocyanates, and chain extending the obtained intermediate with carboxylic acid-capped molecules, to methods for the preparation of such polymeric materials and products such as biomedical articles derived therefrom.

There is a wide variety of materials which are foreign to the human body and which are used in direct contact with its organs, tissues and fluids. These materials are called Biomaterials. With the development of synthetic polymers, approximately one hundred years ago, physicians found available, for the first time, materials which were light, strong, relatively inert and easily fabricated, for use in a wide range of biomedical applications.

The concept of Biocompatibility relates to the quality of the biological performance of biomaterials. In addition to macroscopic function parameters, the interactions developed between the implanted device and its biological environment, play a crucial role. It is now consensual among researchers in the Biomaterials field, that the term "biocompatibility" and "biological performance" have no real meaning, unless they are related to a specific application and a given physiological environment. A variety of implanted devices now exists addressing needs in such diverse areas as cardiovascular surgery, ophthalmology, dentistry, orthopedics and gynecology, each area posing its own particular biocompatibility requirements.

Since materials are not universally biocompatible, the quality of their biological performance will depend on the implantation site and the specificity of the biological conditions under which they are called upon to perform. Nevertheless, and despite the impressive progress in Biomaterials Science, this more advanced conceptual development framework is seldom applied. Biomaterials are still being used, irrespective in most cases of the peculiarity and complexities of each clinical application. Furthermore, to date most polymeric biomaterials are substances that were initially developed by industry for general purposes and that found their way into the biomedical world.

Even though current Biomaterials have contributed significantly to modern medicine, only a new generation of devices, based on novel, tailor-made materials, will permit further progress. They should be developed on the premise that the different aspects of their intended performance—functional as well as biological must be fully integrated into the design and synthesis processes. This should be achieved by incorporating, at a molecular level, features specifically selected for any given biomedical system.

According to the present invention there is now provided a novel family of segmented polyurethanes by applying the approach outlined above.

Polyurethanes are one of the most promising and versatile biomedical polymers. These elastomeric block copolymers comprise, alternatively, hard and soft segments, and exhibit a phase segregated microstructure. The interest these materials have awakened stems mainly from their very good mechanical properties, especially tensile strength and flex fatigue (J. W. Boretos. Pure & Appl. Chem. 52, 1851 (1980); B. D. Ratner, in: Physicochemical Aspects of Polymer Surfaces (K. L. Mittal. Ed.), Plenum Publishing Corp.. New York, 2, 969 (1983): M. Szycher and V. L. Poirier. Ind. Eng. Chemn. Prod. Dev. 22. 588 (1983)) and their enchanced biocompatibility (D. J. Lyman, D. Albo, R. Jackson and K. Knutson, Trans. Am. Soc. Int. Organs 23, 253 (1977): E. W. Merrill, E. W. Salzman, S. Wan, N. Mahmud, L. Kushner, J. N. Lindon and J. Currnie, Trans. Am. Soc. Artif. Organs 28, 482 (1982): E. Nyilas, J. Biomed. Mater. Res. Symp. 3, 97 (1972); S. R. Hanson, L. A. Harker, B. D. Ratner and A. S. Hoffman, J. Lab. Clin. Med. 95, 189 (1980): J. W. Boretos, W. S. Pierce, R. E. Baier, A. F. Leroy and H. J. Donachy, J. Biomed. Mater. Res. 9, 327 (1975)).

These polymers have been considered for various applications such as the artificial heart, arterial prostheses, Pacemaker leads, wound dressings and catheters (J. W. Boretos, Concise Guide to Biomedical Polymers, Thomas, Springfield, Ill. (1973)): J. W. Boretos and W. S. Pierce. Science 158, 1481 (1967); T. Kolff. G. Burkett and J. Feyen, Biomat. Med. Dev., Art. Org. 1(4), 669 (1973); E. Nyilas, U.S. Pat. No. 3,562,352; P. I. Singh and D. Lederman, Implantable Left Heart Assist Device, Annual Report Contract No. NO1-HV-02913. NHLBI-DTB. Bethesda, Md. (1982).

However, due to the rather demanding and diverse requirements biomedical polymers have to comply with, it has long been recognized that a need exists for new elastomeric polymers, exhibiting the advantageous properties of strength, flexibility and extensibility, and biocompatibility, as defined by any given, specific biomedical application. This can be illustrated by the fact that, even though polyurethane elastomers are known for their relatively satisfactory hemo-compatibility, when compared to other materials, post-implantation anticoagulant treatments (e.g. with heparin) are mandatory.

The chemistry involved in the synthesis of polyurethane elastomers centers around the reactions of the isocyanate group. The electronic structure of the resonative forms of the isocyanate functionality, readily explains its chemical activity which is mainly due to the sensitivity of the carbon atom toward nucleophilic attack.

The insertion across the C=N bond is the most important reaction involving isocyanates (S. Patai, The Chemistry of Cyanates and their Thio Derivatives, Parts 1 and 2, The Chemistry of Functional Groups Series, John Wiley & Sons, New York (1969)). This is the basis of polyurethanes synthesis. The reaction proceeds via the attack of a nucleophile species—the oxygen atom in the case of alcohols—at the electrophilic carbon atom in the isocyanate group, whereby a urethane function is formed. The reaction with water is a special case of the same general mechanism, yielding carbon dioxide; this phenomenon is especially useful in the production of foams. When isocyanates react with amine groups, in a reaction significantly faster than the previous one due to the higher nucleophilicity of the nitrogen atom, urea groups are formed.

The urethane formation reaction is largely influenced by the reaction conditions and the catalyst used. The insertion reaction in urethane synthesis is normally catalyzed by alkyl tin compounds or tertiary amines, the former being more effective for producing elastomeric polyurethanes (S. L. Reegan and K. C. Frisch, Adv. Urethane Sci. Technol. 1, 1 (1971)). Furthermore, tin catalysts are specific toward the hydroxyl-isocyanate reaction, whereas tertiary amines catalyze both the hydroxyl-isocyanate as well as the water-isocyanate reactions (L. R. Brecker, Plast. Engr. 33(3), 39 (1977)).

The two most widely used isocyanates in industrial polyurethane synthesis are toluene diisocyanate (TDI) and methylene bis(p-phenyl isocyanate) called also 4,4'-diphenylmethane diisocyanate (MDI). The latter is not only more reactive, but also the polymers containing MDI generally exhibit better physical properties. Typical aliphatic isocyanates include 1,6-hexane diisocyanate (HDI), methylene bis(p cyclohexyl isocyanate) ($H_{12}MDI$) and isophorone diisocyanate (IPDI).

Polyurethanes comprising aliphatic isocyanates possess higher hydrolytic and thermal stability, but this often results in a polymer displaying lower mechanical properties.

Most commercially available polyurethanes comprise relatively short hydroxyl-terminated polyether or polyester soft segments, in the 600 to 6000 g/mol molecular weight range. The three most important polyether glycols used are polyethylene oxide (PEO), polypropylene oxide (PPO) and polytretamethylene oxide (PTMO) chains, normally in the 600 to 2000 molecular weight range. The properties of the different polyurethanes will be largely affected by the chemistry, morphology and molecular weight of the polyether glycol incorporated into the polymeric chain (K. C. Frisch, Rubber Chem. Technol. 45, 1442 (1972)).

When equimolar quantities of diisocyanate and macrodiol are reacted, a polyurethane displaying very poor mechanical properties is obtained. The use of a low molecular weight difunctional molecule, which reacting with the macro-diisocyanate acts as a chain extender, produces high molecular weight polyurethanes, characterized by improved mechanical properties and a two-phase microstructure.

Chain extenders can be classified into two general categories: aliphatic and aromatic diamines and the corresponding diol analogs. Since chain extending with diamines creates urea functionalities along the polymeric backbone. polyurethaneurea polymers are obtained. Expectedly, aliphatic chain extenders usually yield more flexible and softer polymers (C. M. Brunette, S. L. Hsu, W. J. MacKnight and N. S. Schneider. Polym. Eng. Sci. 31, 163 (1981)) due to the stiffness associated with the aromatic ring. Also, the incorporation of aromatic chain extenders generally results in polyurethane matrices comprising larger hard blocks volume fractions. Polyurethanes extended with diamines tend to exhibit better properties than the analog polymer, extended with a diol (C. M. Brunette, S. L. Hsu, W. J. MacKnight and N. S. Schneider, Polym. Eng. Sci. 21, 163 (1981)). It should be stressed, however, that due to their stronger hydrogen bonds and better developed hard domains, polyurethaneureas dissolve with difficulty in most solvents: they are also more difficult to process in the melt state. Since crystalline hard blocks render the polymer with enhanced physical properties, their crystallizability plays an important role. Therefore, the ability of the chain extender to create significant hydrogen bonds, as well as its stiffness and various spatial parameters such as its symmetry and length, will largely affect the characteristics of the polyurethane matrix generated (R. Bonart, L. Morbitzer and H. Rinke, Kolloid Z. Z. Polym. 240, 807 (1970)). Chain extenders commonly used commerically include butanediol (BDO). ethylene diamine (EDA). 4,4'-methylene bis(2-chloraniline (MOCA), ethylene glycol and hexane diol. Also water is sometimes used as chain extender.

The ratio between the macroglycol soft segment and the diisocyanate/chain extender hard block can be varied, to generate polyurethanes covering a wide range of physical and mechanical properties.

Polyurethanes are commonly synthesized by the so called "prepolymer method", in which the polymer is formed in two stages. The first step consists of reacting the diisocyanate and macroglycol, in a 1 stoichiometric ratio, to produce a low molecular weight prepolymer, as shown below:

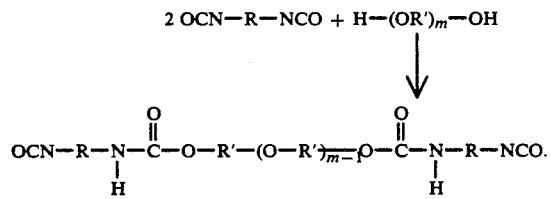

The molecular weight of this oligomeric intermediate will vary within the 1000 to 5000 range, this being mainly determined by the length of the soft segment.

In the next stage the prepolymer is chain extended by reacting with diamines or diols, and producing the high molecular weight polyurethane chain. This second step is illustrated for diamines, in the following reaction:

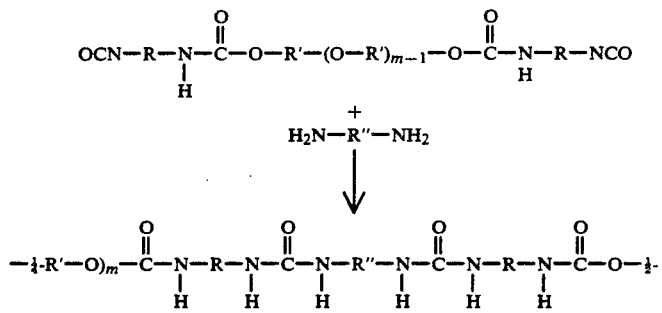

Alternatively, the reaction can be performed in one step, but the properties of the polymer obtained are significantly inferior to those of the polyurethane synthesized step by step.

Thermoplastic elastomers are polymers characterized by rubber-like elasticity, even though they are not covalently crosslinked (L. R. G. Treloar, Rubber Chem. Technol 47(3), 625 (1974)). These macromolecules consist of glassy or crystalline hard blocks, dispersed in an amorphous matrix composed mainly by flexible soft segments. The unique feature of these polymers is that the macromolecular chains comprise two segments, which are chemically incompatible at service temperature. The positive heat of mixing characteristic of these segmented copolymers, is the driving force promoting phase separation processes. The fundamental mechanical function of the flexible segments is to provide the elastic response to the polymeric system. The hard blocks, on the other hand, create sites for secondary intermolecular bonding, forming generally well defined domains; from a mechanical point of view, the hard domains act as multifunctional physical crosslinks and reinforcing fillers.

The two-phase microstructure, typical of most polyurethane elastomers, is accountable for their improved mechanical characteristics, most importantly, their high strength and enhanced flex-fatigue properties. The behavior of these matrices under mechanical stresses will be significantly influenced by the size, concentration and internal cohesive strength of the hard domains. Additional factors are the ability of the segments to become oriented under external load and their crystallizability with strain (S. L. Agarwal, R. A. Livigni, L. F. Marker and T. J. Dudek, in Block and Graft Copolymers (J. J. Burke and V. Weiss, Eds.) Syracuse University Press. Syracuse, N.Y. 157 (1973); T. L. Smith, Polym. Sci. Phys., 12, 1825 (1974). Among the factors influencing the extent of phase segregation in polurethane matrices, it is worth mentioning the ability of the system to create intermolecular hydrogen bonds, usually between the urethane functionality and the carbonyl or ether groups. The segmental molecular weight and crystallizability, as well as the thermal and mechanical history of the polymer, play also an important role. The properties of polyurethane elastomers will be markedly affected by the structure of the diisocyanate, due to its influence on the packing of the hard blocks and the strength of their intermolecular association (R. Bonart, L. Morbitzer and H. Muller, J. Macromol. Sci., Phys. 3(2). 237 (1973)).

Generally, diamine chain extenders generate polyurethanes exhibiting better mechanical properties than their diol-containing analogs. The behavior encountered has been attributed to the ability of urea groups to create stronger intermolecular hydrogen bonds, leading to mutually insoluble soft and hard blocks, a phenomenon which, in turn, results in a microsegregated matrix of enhanced physical characteristics (R. Bonart, L. Morbitzer and H. Muller, J. Macromol. Sci. Phys. 3(2), 237 (1973); R. Bonart, J. Macromol. Sci. Phys. 2(1). 115 (1968)). Since the chain extender can effectively interfere in the spatial hard domains array, its symmetry will have a pronounced effect on the extent to which hard block crystallization processes are promoted, hindered or prevented.

Due to their high reactivity, many diamines are too reactive for use as chain extenders, especially under bulk polymerization conditions. In some of these systems, the reaction is too fast, resulting in premature gelation, before appropriate mixing and homogenization of the reacting mixture is achieved. The extent to which the properties of the polyurethane matrix depend on even minor variations in the structure of the components, can be illustrated by the fact that even the number of carbon atoms in the chain extender molecule, largely affects the resulting matrix. Specifically, it has been shown that when an aliphatic diamine chain extender comprises an odd number of carbon atoms in the chain, improved mechanical properties are obtained (R. Bonart, L. Morbitzer and H. Rinke. Kolloid-Z 240, 807 (1970)). A similar behavior was found for diol-extended polyurethanes (C. M. Brunette, S. L. Hsu, M. Rossman, W. J. MacKnight and N. S. Schneider, Polym. Eng. Sci. 21(11), 668 (1981): B. F. Goodrich Co., British Patent 1025970 (15.7.63)).

Clearly, stiffer and more symmetric molecules, having the ability to form strong and stable intermolecular hydrogen bonds will perform as superior chain extenders. Their incorporation into the polyurethane backbone will result in stronger physical networks, and consequently in polymers exhibiting improved mechanical properties.

There have been various prior art suggestions for modifying polyurethanes, such as incorporating special soft segments such as hydroxyl-capped polyalkyls, e.g. polybutadiene (C. M. Brunette, S. L. Hsu, M. Rossman. W. J. MacKnight and N. S. Schneider, Polym. Eng. Sci. (11), 668 (1981): K. Ono. H. Shimadu. T. Nishimuro, S. Yamashita, H. Okamoto and Y. Minoura. J. Appl. Polym. Sci. 21 3223 (1977)): polyisobutylene (J. P. Dole-Robbe, Bull. Soc. Chim. Fr. 3, 1978 (1973)), polysiloxanes such as short polydimethylsiloxane (P. Chaumont, G. Beinert. J. Herz and P. Rempp, Polymer 22, 663 (1981): S. W. Graham and D. M. Hercules, J. Biomed. Mater. Sci. 15, 349 (1981)). Ger. Offen. DE 2852785 and Ger. Offen. DE 2916545 disclose the preparation of anthranilic acid esters of polyoxyethylated carboxylic acid amides and their use as chain extenders in polyurethanes. Important polyurethane-based polymers developed in recent years include the grafting of poly(amido-amines) chains onto polyurethane backbones, rendering the system with enhanced blood compatibility, due to the ability of the grafted chains to create stable complexes with heparin (R. Barbucci, G. Cassini. P. Ferruti, F. Tempesti, Surface-grafted heparinizable materials, Polymer 26, 1349–1352 (1985)). Also, a new polyurethane-containing system was produced by Barbucci and coworkers (R. Barbucci, P. Ferruti, A. Grossi, W. G. Lemm, Synthetic material apt to stably adsorb high quantities of heparin and process for the production thereof. European Patent 87100478.4) whereby commercially available polyurethanes and poly(amido-amine) chains are bonded via hexamethylene diisocyanate. Important polymeric systems exhibiting enhanced hemo-compatibility developed in recent years include another heparinizable polyurethane developed by M. C. Tanzi and collaborators (M. C. Tanzi, M. Levi. M. Muttoni and G. Tieghi, New Biocompatible Materials: Heparinizable segmented polyurethanes, Second International Conference on Polyurethanes in Biomedical Engineering, Stuttgart, June 1986). These novel copolymers were snythesized by reacting isocyanate-terminated macrodiols with amino-terminated poly(amido-amines). Thromboresistant derivatized polyurethanes were synthesized by Eberhart and his group (M. S. Munro, R. C. Eberhart. N. J. Maki, B. E. Brink, W. J. Fry, Thromboresistant Alkyl Derivatized polyurethanes. ASAIO J., 6. 65-75 (1983)). More recently, similar polyurethanes were prepared following the same basic approach (T. G. Grasel, J. A. Pierce, S. L. Cooper, Effects of alkyl grafting on surface properties and blood compatibility of Polyurethane block copolymers, 12th Meeting of the Society for Biomaterials, Minneapolis, 1986).

According to the present invention there are now provided new and useful synthetic polyurethane-based polymeric materials, derived from reacting flexible diol chains with diisocyanates, and chain extending the obtained intermediate with carboxylic acid-capped molecules. The invention is also directed to methods for the preparation of such polymeric materials and products such as biomedical articles derived therefrom. Thus the present invention provides synthetic polymers having unique and desirable properties.

More specifically, the present invention provides polyurethane-based polymers from which can be manufactured biomedical articles such as sutures, ligatures, wound and burn dressings, membranes, catheters, oesophageal prostheses, vascular grafts, intra-aortic balloons, pacemaker leads tracheal prostheses and intragastric balloons possessing the desired characteristics of flexibility, strength, biocompatibility and sterilizability. Such is achieved, according to the invention, by reacting diverse hydroxy-ended flexible chains, most preferably poly(alkylene glycols) of various molecular weights, with different diisocyanates, and incorporating dicarboxylic acids as a new type of chain extender into the polymeric backbone, to produce segmented copolymers possessing increased flexibility and strength and exhibiting enhanced biocompatibility. The ability shown by the amide groups, produced by the reaction between the isocyanate and carboxylic functionalities, to form strong intermolecular hydrogen bonds, results in well developed hard domains and, in turn, in polymeric materials displaying improved mechanical properties. The enhanced stiffness and planarity associated with the amide group, due to its resonance structures and the consequent partial double bond nature of the C—N linkage is an additional advantageous feature of the chain extenders now provided. A number of polyurethene backbones were developed, most importantly chain extended by maleic or fumaric acid. This significantly affects the morphology of the matrix, resulting in enhanced micro-phase segregation and improved mechanical properties. The new polyurethane-based, double bond-containing polymers will be referred to hereinafter as polyurethenes. The presence of the stiff and planar double bond structure, creating a conjugated system with the amide groups, substantially contributes to the crystallizability of the hard blocks. In addition to their effect on the mechanical properties of the polymeric matrix, the reactive double bonds can serve as binding sites for further derivatization of the polymer. Therefore, the polyurethene chains can serve as the basic scaffold for more complex polymeric systems, incorporating molecules bearing biological relevance. Furthermore, since the material-tissue interface very much determines the overall performance of the biomedical device, the potential for specific surface tailoring is an additional built-in feature of these novel materials, not available with the polyurethanes of the prior art. Thus, guided by biological criteria derived from their specific clinical use, these polymers were surface or bulk tailored to improve their overall performance and/or optimize their interaction with their biological environment.

Thus according to the present invention there are now provided polyurethane-amides selected from: a) a segmented block polyurethane amide (PEUAm) of the following repeating unit [I]

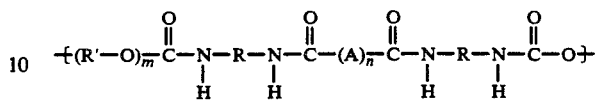

wherein R is hexamethylene, 4,4-diphenylmethane, toluene, naphthalene, 4,4-dicyclohexylmethane, cyclohexyl. 3,3'-dimethylphenyl, 3,3'-dimethyl-diphenylmethane, 4,6'-xylylene, 3,5,5-trimethylcyclohexyl, 2,2,4-trimethyl-hexamethylene or p-phenylene.

R' is selected from a linear or branched, unsubstituted or substituted hydrocarbyl group, said substituents being selected from halogen or hydroxy, or R' is a bivalent Si—($R_1R_2$) group, wherein $R_1$ and $R_2$ are identical or different groups selected from hydrogen, alkyl, a double bond-containing hydrocarbyl group, halogen, hydroxy or an aromatic ring-containing group, and m is a positive integer, A is a bivalent saturated or unsaturated, linear or branched, substituted or unsubstituted hydrocarbyl group, said substituents being selected from halogen, hydroxy, cyano, carboxy or amino groups: or A is an unsubstituted or substituted aromatic ring-containing group, said substituents being selected from halogen, hydroxy, cyano, carboxy or amino groups, and n is zero or a positive integer;

b) a segmented block polyurethane amide of the following repeating unit [II]

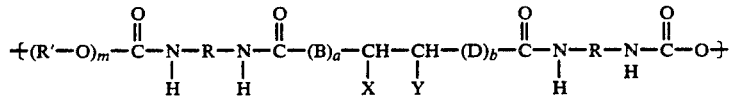

wherein R is hexamethylene, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl. 2,2,4-trimethyl-hexamethylene or p-phenylene, R' is selected from a linear or branched, unsubstituted or substituted hydrocarbyl group, said substitutents being selected from halogen or hydroxy, or R' is a bivalent Si—($R_1R_2$) group, wherein $R_1$ and $R_2$ are identical or different groups selected from hydrogen, alkyl, a double bond-containing hydrocarbyl group, halogen, hydroxy or an aromatic ring-containing group, and m is a positive integer and B and D are each a bivalent, saturated or unsaturated, linear or branched, unsubstituted or substituted hydrocarbyl group, said substituents being selected from halogen, hydroxy, cyano, carboxy or amino groups, or B and D are each an unsubstituted or substituted aromatic ring-containing group, said substituents being selected from halogen, cyano, carboxy or amino groups wherein B and D can be the same or different, and a and b are identical or different and are each 0 or 1, and X and Y are identical or different grafted substituents, usually bearing biomedical relevance.

The term aromatic ring-containing group as used herein is especially directed to aryl groups such as phenyl and substituted phenyl.

The term a double bond-containing hydrocarbyl group is used to designate such groups as vinyl, allyl, etc.

The segmented copolymers of this invention are obtained by reacting diverse hydroxy-ended flexible chains, most preferably poly(alkylene glycols) of various molecular weights, with different diisocyanates, and incorporating a new type of chain extenders, carboxylic acid-capped molecules, (most preferably unsaturated dicarboxylic acids) into the polymeric backbone, to produce segmented copolymers possessing increased flexibility and strength and exhibiting enhanced biocompatibility.

The polymers of this invention are synthesized by a two-stage method, where the first step consists of reacting a diisocyanate having the general formula:

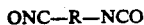

wherein R is hexamethylene, 4,4'-diphenylmethane, toluene, naphthalene, 4,4 -dicyclohexylmethane, cyclohexyl, 3,3'-dimethylphenyl, 3,3 -dimethyl-diphenylmethane, 4,6'-xylylene, 3,5,5-trimethylcyclohexyl, 2,2,4-trimethyl-hexamethylene or p-phenylene, or other short molecules capped by two diisocyanate compounds of the above formula and a macroglycol, most preferably poly(alkylene glycols) of various molecular weights, of the formula:

wherein R' is an alkylene group such as ethylene, propylene, butylene or combinations of them, in a 2:1 stoichiometric ratio, usually in the presence of an urethanization. Promoting catalyst such as dibutyl dilaurate, to produce a low molecular weight prepolymer: the molecular weight of this oligomeric intermediate varies within the 1000 to 5000 range, especially as a function of the length of the hydroxy-ended flexible chains.

During this first step of the reaction, an ABA triblock polymer is formed, its overall molecular weight being essentially determined by the molecular weight of the hydroxy-capped chains. A particularly preferred diisocyanate is hexamethylene diisocyanate (HDI) and a particularly preferred hydroxy-capped chain is polytetramethylene glycol (PTMG) preferably in the 600–2000 molecular weight range. Therefore, the following description and first examples, which are presented by way of illustration, are directed primarily to the synthesis of segmented copolymers comprising hexamethylene diisocyanate (HDI) and polytetramethylene glycol (PTMG) chains, it being understood that certain variations may apply to other diisocyanates and hydroxy-capped chains encompassed by the general formula of the invention (described in less detail in later examples) as will be readily apparent to those skilled in the art.

The ABA triblock oligomer formed at the first stage of the polymerization reaction is exemplified for hexamethylene diisocyanate (HDI) and polytetramethylene glycol (PTMG), reacting in a 2:1 stoichiometric ratio:

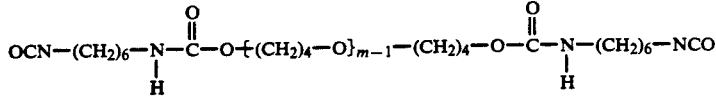

wherein m is a positive integer.

Additional diisocyanates used are 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,24-trimethyl-hexamethylene and p-phenylene, or other short molecules capped by two diisocyanate compounds of the above formula. Additional dihydroxy compounds that can be used include various poly(alkylene glycol) chains such as polyethylene glycol and polypropylene glycol of different molecular weights, and also ethylene glycol; 1,3-propanediol: 1,4-butanediol; 1.5-pentanediol: 1,6-hexanediol; 1,7-heptanediol; 1,8-octanediol: 1,9-nonanediol; 1,10-decanediol; 1,11-undecanediol; 1,12-dodecanediol; 1,13-tridecanediol; 1,14-tetradecanediol; 1,15-pentadecanediol; 1,16-hexadecanediol; oxaaliphatic diols, diaminediol, hydroxy-terminated polydimethyl siloxane polymers and copolymers, fluorinated polyether glycols and poly(butadiene, hydroxyl terminated).

The reaction is carried out in dry solvents such as tetrahydrofuran or dimethylformamide.

In the next stage, the polymers of this invention are obtained by chain extending the prepolymer by reacting the isocyanate groups of the isocyanate-terminated triblock with a compound selected from a group consisting of carboxylic acid-capped chain extenders. Thus e.g. the invention provides copolymeric chains, as exemplified for HDI and PTMO, of the following repeating unit:

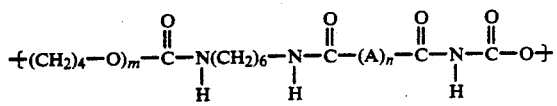

where the isocyanate-terminated triblock copolymers has been chain extended by compounds of the general formula,

as previously defined.

Dicarboxylic acid compounds useful in the synthesis of polymers by the above method include oxalic acid; malonic acid: succinic acid; 2,3-dimethylsuccinic acid: glutaric acid; 3,3-dimethylglutaric acid: adipic acid; 3-methyladipic acid; pimelic acid: suberic acid: azelaic acid; sebacic acid; 1,9-nonanedicarboxylic acid: 1,10-decanedicarboxylic acid; 1,11-undecanedicarboxylic acid; 1,12-dodecanedicarboxylic acid; 1,13-tridecanedicarboxylic acid: 1,14-tetradecanedicarboxylic acid; 1,15-pentadecanedicarboxylic acid; 1,16-hexadecanedicarboxylic acid; maleic acid; trans-beta-hydromuconic acid; fumaric acid; diglycolic acid: 3,3'-oxydipropionic acid: 4,4'-oxydibutiric acid; 5,5'-oxydivaleric acid; 6,6-oxydicaproic acid; 8,8'-oxydicaprilic acid; 6-oxaundecanoic acid: 5-oxaazelaic acid: 5-oxasebacic acid; 5-oxaundecanoic acid; 5-oxadodecanoic acid; 5,oxatetradecanenoic acid; 5-oxahexadecanoic acid; 6-oxadodecanedioic acid: 6-oxa-tridecanedioic acid: 6-oxapentadecanedioic acid: 6-oxaheptadecanedioic acid; 7-oxapentadecanedioic acid; 10-oxanonadecanedioic acid and other oxa-aliphatic dicarboxylic acids; phtalic acid; isophtalic acid; terphthalic and other aromatic dicarboxylic acids; 1,2-cyclobutanedicarboxylic acid; 1,4-cyclohexanedicarboxylic acid; poly(butadiene, carboxyl terminated), poly(oxyalkylene, carboxyl terminated); carboxy-ended polydimethyl siloxane polymers and copolymers and halogen, hydroxy, amino or cyano-containing dicarboxylic acids.

Thus in a first aspect of the present invention there is now provided biomedical articles comprised of: a segmented block polyurethane amide (PEUAm) of the following repeating unit I]

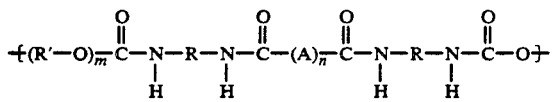

wherein R is hexamethylene, 4,4'-diphenylmethane, toluene, naphthalene, 4,4'-dicyclohexylmethane, cyclohexyl, 3,3'-dimethylphenyl. 3,3'-dimethyl-diphenylmethane, 4,6'-xylylene, 3,5,5-trimethylcyclohexyl, 2,2,4-trimethyl-hexamethylene or p-phenylene.

R' is selected from a linear or branched, unsubstituted or substituted hydrocarbyl group, said substituents being selected from halogen or hydroxy, or R' is a bivalent Si—($R_1R_2$) group, wherein $R_1$ and $R_2$ are identical or different groups selected from hydrogen, alkyl, a double bond-containing hydrocarbyl group, halogen, hydroxy or an aromatic ring-containing group, and m is a positive integer.

A is a bivalent saturated or unsaturated, linear or branched, substituted or unsubstituted hydrocarbyl group, said substituents being selected from halogen, hydroxy, cyano, carboxy or amino groups; or A is an unsubstituted or substituted aromatic ring-containing group, said substituents being selected from halogen, hydroxy, cyano, carboxy or amino groups, and n is zero or a positive integer.

In another preferred aspect of the present invention there is provided a polyurethane amide segmented copolymer useful for the manufacture of biomedical articles, having a general repeating unit II]

a segmented block polyurethane of the following repeating unit [II]

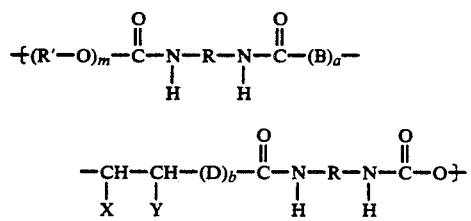

wherein R is hexamethylene, 4,4'-diphenylmethane, toluene, naphthalene, 4,4'-dicyclohexylmethane, cyclohexyl, 3,3'-dimethylphenyl, 3,3'-dimethyl-diphenylmethane, xylylene, 3,5,5-trimethylcyclohexyl, 2,2,4-trimethyl-hexamethylene or p-phenylene.

R is selected from a linear or branched, unsubstituted or substituted hydrocarbyl group, said substitutents being selected from halogen or hydroxy, or R' is a bivalent Si—($R_1R_2$) group, wherein $R_1$ and R2 are identical or different groups selected from hydrogen, alkyl, a double bond-containing hydrocarbyl group, halogen, hydroxy or an aromatic ring-containing group, and m is a positive integer and B and D are each a bivalent, saturated or unsaturated, linear or branched, unsubstituted or substituted hydrocarbyl group, said substituents being selected from halogen, hydroxy, cyano, carboxy or amino groups, or B and D are each an unsubstituted or substituted aromatic ring-containing group, said substituents being selected from halogen. cyano, carboxy or amino groups wherein B and D can be the same or different, and a and b are identical or different and are each 0 or 1, and X and Y are identical or different grafted substituents, usually bearing biomedical relevance.

In the above polyurethane amide segmented copolymers, X and Y may be the same or different and each is a monomer selected from 2-hydroxyethyl methacrylate, acrylic acid, acrylamide, methyl methacrylate, pentafluorobutyl acrylate, pentamethyl disiloxanylmethyl methacrylate or acrylonitrile or X and Y are the same or different and each is a polyethylene glycol chain which prevents irreversible protein adsorption on surfaces, or X and Y are the same or different and each is a poly(amido-amine) chain which renders the system with enhanced blood compatibility due to its ability to form stable complexes with heparin or X and Y are the same or different and each is a $C_{16}$ or $C_{18}$ alkyl chain, the resulting surface being characterized by selective albumin affinity.

In preferred embodiments of the present invention X and Y are the same or different and each is selected from poly(2-hydroxyethyl methacrylate) chains, polyacrylamide chains, polymethyl methacrylate chains, polyacrylic acid chains, poly(perfluoroalkyl methacrylate) chains, poly(pentamethyl disiloxanylmethyl methacrylate) chains, amino-terminated polyethylene oxide chains, hexadecane or octadecane chains, poly)amidoamine) chains or from biodegradable chains selected from polyglycolic acid, polyactic acid or polyethylene glycol/polylactic acid block copolymers.

In these preferred embodiments the grafted chains perform as spacers for binding biologically active molecules selected from enzymes, antibiotics and anti-thrombogenic agents, onto the surface and/or bulk of the polymeric system. Thus in preferred embodiments of the present invention X and Y are the same or different and each is a biodegradably polyglycolic acid, polylactic acid or polyethylene glycol/polylactic acid block copolymer, temporarily bound to a biologically active molecule selected from an enzyme, antibiotic, hormone, or anti-thrombogenic agent whereby the system performs as a controlled delivery system.

The polyurethanes of formula [II]comprise unsaturated chain extenders of the general formula [III]

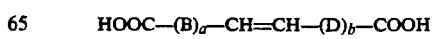

wherein B and D are each an unsubstituted or substituted aromatic ring-containing group, said substituents being selected from halogen, cyano, carboxy or amino groups wherein B and D can be the same or different, and a and b are identical or different and are each 0 or 1.

The molecules grafted onto the active double bond introduced into the polyurethene backbone via the incorporation of an unsaturated dicarboxylic acid, such as maleic acid or fumaric acid, differ substantially as a function of the specific clinical application of the polymeric system.

Various reactions were used to derivatize the basic polyurethene matrices. Preferred examples of these reactions are the following:

(1) grafting of active monomers onto the double bond, via a conventional addition polymerization mechanism, and (2) nucleophilic attack of appropriate agents (e.g. amines) on Michael-type substrates, such as the polyurethene olefinic double bond, which is conjugated with, and activated by electronegative unsaturated moities. The derivatization of the polymeric matrix can be exemplified by the grafting of 2-hydroxyethyl methacrylate (HEMA) for the first type of reaction, and by the addition of amino-terminated polyethylene oxide chains, for the second type of reaction. Clearly, these reactions may result, not only in grafting pendant groups onto the backbone, but also crosslinked matrices may be generated. Whether a thermoplastic or a thermoset system is obtained, will depend on the functionality, the molecular weight and the flexibility of the grafting molecule, as well as on several experimental parameters. Further examples of the derivatization of the system, useful in the invention may advantageously comprise, among others, epoxydation, hydroylation and halogenation reactions.

As indicated hereinbefore the polymers of the invention find advantageous utility in the manufacture of biomedical articles and pharmaceutical compositions as is known in the art of polymers in living systems. Thus, the present invention also provides biomedical articles including a suture or ligature, particularly in the form of flexible monofilaments, a suture in the form of a needle and a suture combination, a surgical clip or staple, a surgical prosthesis, a vascular graft, wound and burn coverings, membranes, catheters, oesophageal prostheses, intra-aortic balloons, pacemaker leads, tracheal prostheses and intra-gastric balloons, textile structures, couplings, tubes, supports, pins, screws or other forms of support. Yet further objects of this invention include a self-supporting film, hollow tube, beads or gel, containing a uniformly dispersed drug for controlled continuous administration, manufactured from polymers of the present invention.

The polymeric materials of this invention can be fabricated into films and fibers by melt extrusion. The polymers of the present invention are also useful in the manufacture of cast and/or extruded films and molded solid surgical aids and biomedical devices. The polymers are melt extruded through a spinneret in a conventional manner to for one or more filaments which are subsequently drawn about three to six times in order to achieve molecular orientation and improve tensile properties. The resulting oriented filaments have good tensile and dry knot strength and good in vivo strength retention. To further improve dimensional stability and tensile strength retention, the oriented filaments may be subjected to an annealing treatment, by heating them at various temperatures for different time periods, while preventing the filaments from measurable shrinking.

Fabrics comprising polymeric materials of this invention, alone or in combination with other polymers, have been developed by textile and non-textile techniques. Multicomponent fabrics, woven, knitted, felted, adhesively united or otherwise, comprising at least two different polymers, at least one of them according to the present invention, were prepared. Also fabric tubes having separate strands of bicomponent materials or strands of two separate components, wherein at least one is according to the invention, were produced. A coated fabric, comprising a substantially continuous sheet of a second material or materials was prepared by hot melt coating. A coating from a solvent system or with coating rolls, the base fabric of which may be wholly non-absorbable although it may contain an absorbable component, were produced.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

PREPARATION OF PEUAM COMPRISING HDI/PTMG2000/OXALIC ACID

The segmented polyurethane amide is synthesized by the so-called "prepolymer method", in which the polymer is formed in two stages. The first step consists of reacting hexamethylene diisocyanate (HDI) and polytetramethylene oxide (PTMO), in a 2:1 stoichiometric ratio, to produce a low molecular weight prepolymer. In the next step this oligomeric intermediate is chain extended by reacting with the oxalic acid chain extender.

1.68 gr HDI (10 mmole) were placed in a 500 ml three-necked flask fitted with a mechanical stirrer and a nitrogen flow inlet, together with 100 ml tetrahydrofuran (THF) and 0.2 gr dibutyltin dilaurate (DBTDL). The system was flushed with dry nitrogen and heated up to 70° C. 10 gr PTMO (5 mmole) (MW=2000) were added dropwise during 40 minutes, the reaction being continued for additional 40 minutes. 0.45 gr oxalic acid (5 mmole) and 0.2 gr DBTDL were dissolved in 75 ml THF. and added dropwise to the prepolymer solution during 40 minutes, and the reaction was continued for additional 40 minutes. Finally the polymer was obtained by precipitating it in soft cold water while stirring. After repeated rinsing in water, and thorough drying at 50° C. under vacuum, the polymer was obtained in the form of white and soft flakes.

EXAMPLE 2

PREPARATION OF PEUAM COMPRISING HDI/PTMG2000/MALONIC ACID

The procedure of example 1 was followed using 0.52 gr (5 mmole) malonic acid, to obtain the title compound.

EXAMPLE 3

PREPARATION OF PEUAM COMPRISING HDI/PTMG2000/SUCCINIC ACID

The procedure of example 1 was followed using 0.59 gr (5 mmole) succinic acid, to obtain the title compound.

EXAMPLE 4

PREPARATION OF PEUAM COMPRISING HDI/PTMG2000/GLUTARIC ACID

The procedure of example 1 was followed using 0.66 gr (5 mmole) glutaric acid, to obtain the title compound.

EXAMPLE 5

PREPARATION OF PEUAM COMPRISING HDI/PTMG2000/ADIPIC ACID

The procedure of example 1 was followed using 0.73 gr (5 mmole) adipic acid, to obtain the title compound.

EXAMPLE 6

PREPARATION OF PEUAM COMPRISING HDI/PTMG2000/PIMELIC ACID

The procedure of example 1 was followed using 0.80 gr (5 mmole) pimelic acid to obtain the title compound.

EXAMPLE 7

PREPARATION OF PEUAM COMPRISING HDI/PTMG2000/SEBACIC ACID

The Procedure of example 1 was followed using 1.01 gr (5 mmole) sebacic acid, to obtain the title compound.

EXAMPLE 8

PREPARATION OF PEUAM COMPRISING HDI/PTMG2000/MALEIC ACID

The Procedure of example 1 was followed using 0.58 gr (5 mmole) maleic acid, to obtain the title compound.

EXAMPLE 9

PREPARATION OF POLY(AMIDO-AMINE)-GRAFTED PEUAM COMPRISING HDI/PTMG200/MALEIC ACID

The procedure of example 1 was followed using 0.58 gr (5mmole) maleic acid, to obtain the basic polyurethene backbone. Then, 2 grams PEUAm were placed in a 125 ml flask fitted with a magnetic stirrer, together with 20 ml tetrahydrofuran (THF). The mixture was stirred for 24 hours, until the polymer was completely dissolved, and a clear and homogeneous solution was obtained. 1.6 mmole poly(amido-amine) and 10 ml methanol were added to the polymer solution, and the addition reaction was conducted, with continuous stirring, for 24 hours at room temperature. Next, the grafted polymer was casted on a glass plate, and the solvent was allowed to slowly evaporate at room temperature. Then, the polymeric film was repeatedly rinsed in water and finally dried at 50° C. under vacuum, until constant weight was obtained.

Some properties of the block copolymers produced according to the above examples, are set forth in Table I.

EXAMPLE 10

PREPARATION OF POLY(AMIDO-AMINE) SURFACE GRAFTED ON PEUAM COMPRISING HDI/PTMG2000 MALEIC ACID

The procedure of example 1 was followed using 0.58 gr (5 mmole) maleic acid, to obtain the basic polyurethene backbone. Samples (20 mm×10 mm×0.26 mm) were cut from films casted from 10% polymer solutions in THF. and immersed in a water-methanol (2:1, 0.3% weight solution of the poly amido-amine). The reaction was conducted at 45° C. for 24 hours, when maximum addition to the double bond was attained. Then, the polymeric film was repeatedly rinsed in water and finally dried at 50° C. under vacuum, until constant weight was obtained.

EXAMPLE 11

PREPARATION OF P(HEMA)-GRAFTED PEUAM COMPRISING HDI/PTMG2000/MALEIC ACID

The procedure of example 1 was followed using 0.58 gr (5 mmole) maleic acid, to obtain the basic polyurethene backbone. Then, 2.45 grams PEUAm were placed in a flask together with 250 ml tetrahydrofuran (THF). The mixture was stirred for 24 hours, until the polymer was completely dissolved, and a clear and homogeneous solution was obtained. 1.6 mmole 2-hydroxyethyl methacrylate containing 1% weight bezoyl peroxide as the initiator of the free radical additional mechanism, were added to the polymer solution, and the reaction was conducted for 24 hours at 66° C. Next, the grafted polymer was casted on a glass plate, and the solvent was allowed to slowly evaporate at room temperature. Then, the polymeric film was repeatedly rinsed in acetone and finally dried at 50° C. under vacuum, until constant weight was obtained.

TABLE I

| Properties of PEUAm comprising HDI/PTMG2000/dicarboxylic acid | | | |
|---|---|---|---|
| Carboxylic acid | $T_{gs}$ (°C) | $T_{ms}$ (°C) | $T_h$ (C°) |
| Oxalic | −75 | 11.7 | 191 |
| Malonic | −75 | 18.7 | 282 |
| Succinic | −76 | 11.0 | 278 |
| Glutaric | −75 | 20.0 | 281 |
| Adipic | −80 | 13.5 | 282 |
| Pimelic | −81 | 26.0 | 275 |
| Azelaic | −77 | 11.4 | 281 |
| Sebacic | −76 | 12.9 | 280 |

Solvent cast films were prepared and standard strips for tensile testing were prepared. The mechanical analysis of the polyurethane amide segmented copolymers developed revealed highly flexible materials.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A polyurethane amide segmented copolymer selected from:
   a) a segmented block polyurethane amide (PEUAm) of the following repeating unit [I]

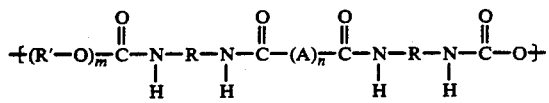

wherein R is hexamethylene, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethyl-hexamethylene or p-phenylene, R' is selected from a linear or branched, unsubstituted or substituted hydrocarbyl group, said substituents being selected from halogen or hydroxy, or R' is a bivalent Si—$(R_1R_2)$ group, wherein $R_1$ and $R_2$ are identical or different groups selected from hydrogen, alkyl, a double bond-containing hydrocarbyl group, halogen, hydroxy or an aromatic ring-containing group, and m is a positive integer, A is a bivalent saturated or unsaturated, linear or branched, substituted or unsubstituted hydrocarbyl group, said substituents being selected from halogen, hydroxy, cyano, carboxy or amino groups; or A is an unsubstituted or substituted aromatic ring-containing group, said substituents being selected from halogen, hydroxy, cyano, carboxy or amino groups, and n is zero or a positive integer:

b) a segmented block polyurethane amide of the following repeating unit [II]

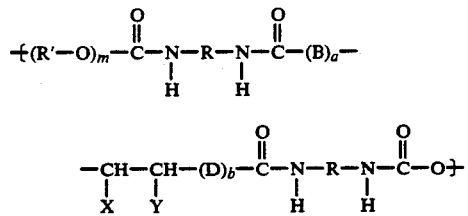

wherein R is hexamethylene. 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethyl-hexamethylene or p-phenylene, R' is selected from a linear or branched, unsubstituted or substituted hydrocarbyl group, said substitutents being selected from halogen or hydroxy, or R' is a bivalent Si—$(R_1R_2)$ group, wherein $R_1$ and $R_2$ are identical or different groups selected from hydrogen, alkyl, a double bond-containing hydrocarbyl group, halogen, hydroxy or an aromatic ring-containing group, and m is a positive integer and B and D are each a bivalent, saturated or unsaturated, linear or branched, unsubstituted or substituted hydrocarbyl group, said substituents being selected from halogen, hydroxy, cyano, carboxy or amino groups, or B and D are each an unsubstituted or substituted aromatic ring-containing group, said substituents being selected from halogen, cyano, carboxy or amino groups wherein B and D can be the same or different, and a and b are identical or different and are each 0 or 1, and X and Y are identical or different grafted substituents, usually bearing biomedical relevance.

2. A polyurethane amide segmented copolymer useful for the manufacture of biomedical articles, having a general repeating unit [I]

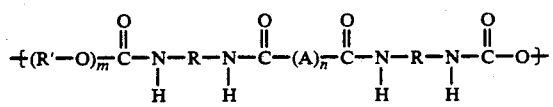

wherein R is hexamethylene, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethyl-hexamethylene or p-phenylene, R' is selected from a linear or branched, unsubstituted or substituted hydrocarbyl group, said substituents being selected from halogen or hydroxy, or R' is a bivalent Si—$(R_1R_2)$ group, wherein $R_1$ and $R_2$ are identical or different groups selected from hydrogen, alkyl, a double bond-containing hydrocarbyl group, halogen, hydroxy or an aromatic ring-containing group, and m is a positive integer, A is a bivalent saturated or unsaturated, linear or branched, substituted or unsubstituted hydrocarbyl group, said substituents being selected from halogen, hydroxy, cyano, carboxy or amino groups, or A is an unsubstituted or substituted aromatic ring-containing group, said substituents being selected from halogen, hydroxy, cyano, carboxy or amino groups, and n is zero or a positive integer.

3. A polyurethane amide segmented copolymer useful for the manufacture of biomedical articles, having a general repeating unit [II]
   b) a segmented block polyurethane of the following repeating unit [II]

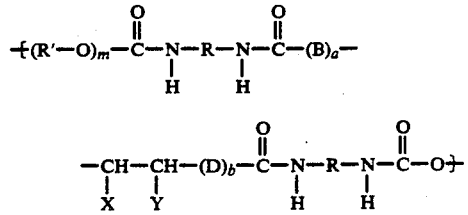

wherein R is hexamethylene, 4,4'-diphenylmethane, toluene, naphthalene, 4,4' dicyclohexylmethane, cyclohexyl, 3,3'-dimethylphenyl, 3,3'- dimethyl-diphenylmethane, 4,6'-xylylene, 3,5,5-trimethylcyclohexyl, 2,2,4-trimethyl-hexamethylene or p-phenylene, R is selected from a linear or branched, unsubstituted or substituted hydrocarbyl group, said substituents being selected from halogen or hydroxy, or R' is a bivalent Si—$(R_1R_2)$ group, wherein $R_1$ and $R_2$ are identical or different groups selected from hydrogen, alkyl, a double bond-containing hydrocarbyl group, halogen, hydroxy or an aromatic ring-containing group, and m is a positive integer and B and D are each a bivalent, saturated or unsaturated, linear or branched, unsubstituted or substituted hydrocarbyl group, said substituents being selected from halogen, hydroxy, cyano, carboxy or amino groups, or B and D are each an unsubstituted or substituted aromatic ring-containing group, said substituents being selected from halogen, cyano, carboxy or amino groups wherein B and D can be the same or different, and a and b are identical or different and are each 0 or 1, and X and Y are identical or different grafted substituents, usually bearing biomedical relevance.

4. A polyurethane amide segmented copolymer as claimed in claim 1 wherein X and Y are the same or different and each is a monomer selected from 2-hydroxyethyl methacrylate, acrylic acid, acrylamide, methyl methacrylate, pentafluorobutyl acrylate, pentamethyl disiloxanylmethyl methacrylate or acrylonitrile.

5. A polyurethane amide segmented copolymer as claimed in claim 1 wherein X and Y are the same or different and each is a polyethylene glycol chain which prevents irreversible protein adsorption on surfaces.

6. A polyurethane amide segmented copolymer as claimed in claim 1 wherein X and Y are the same or different and each is a poly(amido-amine) chain which renders the system with enhanced blood compatibility due to its ability to form stable complexes with heparin.

7. A polyurethane amide segmented copolymer as claimed in claim 1 wherein X and Y are the same or different and each is a $C_{16}$ or $C_{18}$ alkyl chain, the resulting surface being characterized by selective albumin affinity.

8. A polyurethane amide segmented copolymer as claimed in claim 2 where R is selected from hexamethylene. 4,4'-diphenylmethane or 4,4'-dicyclohexylmethane.

9. A polyurethane amide segmented copolymer as claimed in claim 2 where R' is selected from butylene, ethylene, propylene, a Si—$(CH_3)_2$ group, perfluorobutylene, polybutadiene or polyisobutylene.

10. A polyurethane amide segmented copolymer as claimed in claim 2 where the chain extender is selected from oxalic acid, succinic acid, adipic acid, suberic acid, sebacic acid, maleic acid, fumaric acid, terephthalic acid, or trans-beta-hydromuconic acid.

11. A polyurethane amide segmented copolymer as claimed in claim 3 where R is selected from hexamethylene, 4,4'-diphenylmethane or 4,4'-dicyclohexylmethane.

12. A polyurethane amide segmented copolymer as claimed in claim 3 where R' is butylene, ethylene, propylene, Si—$(CH_3)_2$, perflurobutylene, polybutadiene, polyisobutylene.

13. A polyurethane amide segmented copolymer as claimed in claim 3 where the chain extender is selected from maleic acid, fumaric acid or trans-beta-hydromuconic acid.

14. A polyurethane amide segmented copolymer as claimed in claim 3 where X and Y are the same or different and each is selected from poly(2-hydroxyethyl methacrylate) chains, polyacrylamide chains, polymethyl methacrylate chains, polyacrylic acid chains, poly(perfluoroalkyl methacrylate) chains, poly(pentamethyl disiloxanylmethyl methacrylate) chains, amino-terminated polyethylene oxide chains, hexadecane or octadecane chains, poly)amido-amine) chains or from biodegradable chains selected from polyglycolic acid, polyactic acid or polyethylene glycol/polylactic acid block copolymers.

15. A polyurethane amide segmented copolymer as claimed in claim 14 where the grafted chains perform as spacers for binding biologically active molecules selected from enzymes, antibiotics and anti-thrombogenic agents, onto the surface and/or bulk of the polymeric system.

16. A polyurethane amide segmented copolymer as claimed in claim 3 wherein X and Y are the same or different and each is a biodegradably polyglycolic acid, polylactic acid or polyethylene glycol/polylactic acid block copolymer, temporarily bound to a biologically active molecule selected from an enzyme, antibiotic, hormone, or anti-thrombogenic agent whereby the system performs as a controlled delivery system.

17. A polyurethane amide segmented copolymer as claimed in claim 1 wherein said copolymer is in the form of at least one filament.

18. A biomedical article selected from the group consisting of a suture, ligature, needle and suture combination, surgical prosthesis, film, membrane, textile structure, wound and burn dressing, coupling, tube, catheter, a vascular graft, oesophageal prosthesis, intraaortic balloon, pacemaker lead, tracheal prosthesis, physical or biological support, screw or pin, where at least one of the components of each of said articles is a polymer as claimed in claim 1.

19. A compound vascular prosthesis comprising a Polymer or polymers as claimed in claim 1.

20. A compound vascular prosthesis comprising a component selected from polyethylene terephthalate, polyether esters, polydimethyl siloxane polymers or copolymers, biodegradable polyether esters and a polymer or polymers as claimed in claim 1.

21. A selectively biodegradable vascular prosthesis comprising an absorbable component in the form of biodegradable polyether esters and a polymer or polymers as claimed in claim 1.

22. A selectively biodegradable vascular prosthesis manufactured by textile and non-textile techniques, comprising polymers as claimed in claim 1.

23. A wound or burn dressing comprising a polymer or polymers as claimed in claim 1.

24. A selectively biodegradable wound or burn dressing comprising an absorbable component selected from biodegradable polyether esters and a polymer or polymers as claimed in claim 1.

25. A pharmaceutical composition comprising a self-supporting film, hollow fiber, beads or gel, manufactured from a polyurethane amide segmented copolymer or copolymers as claimed in claim 1 and containing a uniformly dispersed drug contained therein.

26. A pharmaceutical composition comprising a self-supporting film, hollow fiber, beads or gel, manufactured from a polyurethane amide segmented copolymer or copolymers as claimed in claim 1(b) and a drug grafted to the polyurethene amide backbone via a spacer selected among biodegradable polymeric chains.

* * * * *